United States Patent [19]
Frazin et al.

[11] Patent Number: 5,546,949
[45] Date of Patent: Aug. 20, 1996

[54] METHOD AND APPARATUS OF LOGICALIZING AND DETERMINING ORIENTATION OF AN INSERTION END OF A PROBE WITHIN A BIOTIC STRUCTURE

[76] Inventors: Leon Frazin, 542 Willgate Ter., Glencoe, Ill. 60027; Michael J. Voresh, 2296 Scott Rd., Northbrook, Ill. 60062

[21] Appl. No.: 406,273

[22] Filed: Mar. 16, 1995

Related U.S. Application Data

[63] Continuation of Ser. No. 233,507, Apr. 26, 1994, abandoned.

[51] Int. Cl.⁶ .................................................. A16B 8/12
[52] U.S. Cl. ........................................................ 128/662.06
[58] Field of Search ................. 128/660.07, 661.07, 128/661.08, 661.09, 661.1, 662.04, 662.06

[56] References Cited

U.S. PATENT DOCUMENTS

| | | |
|---|---|---|
| 4,697,595 | 10/1987 | Breyer et al. . |
| 4,706,681 | 11/1987 | Breyer et al. . |
| 4,821,731 | 4/1989 | Martinelli et al. . |
| 5,054,492 | 10/1991 | Scribner et al. . |
| 5,174,295 | 12/1992 | Christian et al. ................. 128/662.06 |
| 5,203,337 | 4/1993 | Feldman ............................ 128/662.06 |
| 5,425,370 | 6/1995 | Vilkomerson .................... 128/662.06 |

*Primary Examiner*—George Manuel
*Attorney, Agent, or Firm*—Welsh & Katz, Ltd.

[57] ABSTRACT

A method and apparatus is provided for localizing and determining orientation of an insertion end of a probe have diagnostic or therapeutic utility within a biotic structure. The apparatus includes a probe with a directional acoustic transmitter attached to a tip of the catheter and a power supply for energizing the directional acoustic transmitter. The apparatus also includes an ultrasonic imaging system for displaying positional information of the catheter and an orientation indicating representation of a signal from the directional acoustic transmitter.

36 Claims, 1 Drawing Sheet

5,546,949

METHOD AND APPARATUS OF LOGICALIZING AND DETERMINING ORIENTATION OF AN INSERTION END OF A PROBE WITHIN A BIOTIC STRUCTURE

This application is a continuation of U.S. Patent application Ser. No. 08/233,508, which was filed Apr. 26, 1994 and is now abandoned.

FIELD OF INVENTION

The field of the invention relates to probe positioning within the cavities or incorporeal conduits (e.g. cardiovascular systems) of living subjects and in particular to the use of acoustic position sensing of probes within the bodies of such subjects.

BACKGROUND

Catheterization of the cardiovascular system may be performed for any of a number of diagnostic and therapeutic reasons. For example, catheterization may be used to implant electrodes of a pacemaker into the heart of a subject needing a pacemaker or for balloon angioplasty where a balloon is inflated in an artery of a subject thereby widening restricted blood vessels. Catheterization is also useful in relation to certain surgical procedures for the repair of damaged blood vessels. Additionally a host of other medical procedures require incorporeal placement of other invasive devices, and precise knowledge of device position within the body.

One difficulty in performing medical procedures involving catheterization lies in guiding the catheter through blood vessels of the cardiovascular system. As the catheter moves through the blood vessel, the catheter is prone to taking "wrong turns" into secondary blood vessels leading away from the target of the intervention.

To solve the problem of locating a probe such as a catheter within a blood vessel, fluoroscopy has been relied upon in conjunction with the use of an iodine contrast medium introduced into the blood of the subject. Fluoroscopy, in fact, has been used since 1950 in retrograde aortic root and left and right ventricle catheterization and angioplasty for accurate catheter guidance.

Other methods of determining a location of a probe inside blood vessels of the cardiovascular system have included ultrasonic imaging techniques. Using ultrasound, sound waves are transmitted from an ultrasonic transducer through the soft tissue of the subject. Upon striking the probe, the sound waves are reflected back to the ultrasonic transducer where the reflected sound waves are detected and an image of the reflecting object is displayed on a monitor.

Two dimensional ultrasonic images are displayed on the monitor in a pie-shape format. The apex of the pie represents the relative position of the ultrasonic transducer and ultrasonically reflecting objects are displayed radially from the apex with the imaging field. Relative positioning of the reflecting object within the display is determined by the length of time required for a reflected sound wave to return to the transducer and from the relative angle of the sound wave with respect to the transducer.

While ultrasonic imaging can provide important information relative to probe position, it is limited in at least two aspects. First, ultrasound does not easily pass through bone. More to the point, bone reflects ultrasound sufficiently to mask, and thereby render invisible, important structures lying behind the bone.

Secondly, an ultrasound image (e.g., B-mode) is a two-dimensional display, providing information with respect to a small area of a two-dimensional plane passing through the body. Where a catheter passes orthogonally through the plane, the ultrasonic image may display a small circular shape, representative of the diameter of the probe. By moving the ultrasonic transducer, an operator may be able to obtain more information (i.e., by aligning the plane of the ultrasound transducer with a portion of the length of the probe). However, if the probe tube is deflected in more than two dimensions (a highly likely event in most cases) the operator will not be able to identify an insertion end of the probe much less the orientation of the insertion end with respect to the catheterized subject. In addition, some cardiac structures, such as valvular apparatus and aortic wall, especially if highly echogenic, can be mistaken as the catheter tip.

One advance in obtaining the position of the insertion end of the catheter has been provided by U.S. Pat. No. 4,706,681 to Breyer, et al. In Breyer et al. a piezoelectric transducer was placed at the insertion end of the catheter for the transmission of a marker signal to the ultrasonic transducer.

While Breyer et al. is effective in locating the insertion end of the catheter, Breyer et al. still is relatively ineffective in providing information as to the direction in which the catheter end is pointing. When the end of the catheter has doubled over or has entered an incorrect blood vessel, it is still difficult, if not impossible, to identify such conditions. Because of the importance of catheterizations to heart patients, a need exists for an apparatus and method of determining an orientation of a probe within a biotic structure.

SUMMARY OF THE INVENTION

Figure 1:
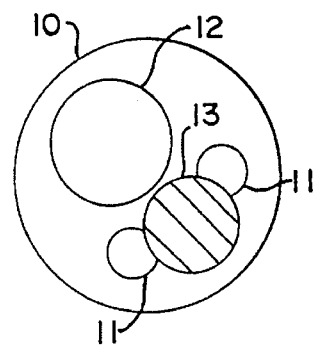
FIG. 1 is an end view of a catheter in accordance with the invention.

A method and apparatus for localizing and determining orientation of an insertion end of a probe having diagnostic or therapeutic utility within a biotic structure. The apparatus includes a probe with a directional acoustic transmitter attached to a tip of an insertion end of the probe. The apparatus also includes an ultrasonic imaging system for displaying positional information of the probe and an orientation indicating representation of a signal from the directional acoustic transmitter.

BRIEF DESCRIPTION OF THE PREFERRED EMBODIMENT

The solution to the problem of determining location and orientation of an insertion end of a probe within the body of a subject (i.e., a blood vessel of a heart patient) lies conceptually in placing a directional acoustical transmitter at the insertion end of the probe and using an acoustic signal of the acoustic transmitter detected by an ultrasonic imaging system as an indication of orientation with respect to a catheterized subject. An associated ultrasonic imaging system is used to detect and display an orientation indicating representation of the signal from the directional acoustic transmitter on the catheter as well as to provide localizing and imaging information. The ultrasonic imaging system displays probe orientation and location on an ultrasonic monitor based upon signals emitted from the directional acoustic transmitter on the probe and from an ultrasonic transducer of the imaging system. An ultrasonic transducer of the ultrasonic imaging system is located in the same plane as the catheter (e.g., on the opposite side of the organ to be catheterized) for receiving signals from the directional acoustic transmitter. The monitor of the ultrasonic transducer, in addition to displaying structures reflecting sound from the transducer of the imaging system, will also display a representation of the signal transmitted by the directional acoustic transmitter. Since the strength of the transmitted signal from the probe to the ultrasonic transducer is a function of the orientation of the directional acoustic transmitter, and distance, changes in the orientation of the probe can be detected by changes in the representation displayed on the ultrasonic monitor.

It is to be understood that the invention described herein may be applicable to a variety of probes and probing techniques including probes having diagnostic and/or therapeutic utility. Within the cardiovascular system the invention may be used for guidance of flow velocity probes, pressure measurement probes, myocardial biopsy devices and for electrode probe placement. The invention may also be used for guidance for catheters enabling the delivery of ultrasound contrast material for purposes of determining organ perfusion. It may be used for guidance for intravascular B-mode imaging devices and for balloon dilation devices. Guidance can also be provided for atherectomy, laser, and rotablation devices. Guidance may be provided for occluder devices such as those used in the treatment of congenital heart disease or acquired intracardiac shunts. Guidance may also be provided for placement of ventricular assist devices.

In the area of OB/GYN, biopsy devices for the breast or chorionic villus may be more accurately located. Aspiration devices for the umbilical cord or amniocentesis are applications.

Gastrointestinal or genitourinary probes for hepatic or kidney or prostate biopsies, respectively, may be more accurately placed under this invention.

Aspiration and biopsy devices for neurosurgical applications are also included.

Under an embodiment of the invention, the directional acoustic transmitter is a piezoelectric element (Doppler acoustic transducer) interconnected with a Doppler standard velocimeter. The velocimeter, in addition to functioning as a power supply in providing an excitation signal to the Doppler transducer, also beneficially serves the function of measuring blood flow during retrograde arterial catheterization. Measurement of blood flow during catheterization ensures the safety of the patient by ensuring that the catheter is advancing in the proper direction. Where the catheter is not advancing in the proper direction (i.e., the catheter has doubled over during insertion) the velocimeter may be used to detect a reversal of blood flow past the Doppler transducer.

The Doppler velocimeter under the embodiment is a Model No. 100 manufactured by Triton Technology of San Francisco, Calif., has a 20 mega Hertz (Mhz) transducer excitation frequency and a pulse repetition frequency of 120 kilo Hertz (Khz). The Doppler velocimeter is constructed to successively transmit eight cycle bursts, each followed by a pause, during which the velocimeter listens for echoes and then determines a blood velocity based on those echoes. The Doppler transducer is a 0.076 mm thick by 1.016 mm diameter piezoelectric crystal supplied by Crystal Biotech of Hopkington, Mass.

The catheter (FIG. 1) used under the embodiment is a three-hole (triple lumen) multipurpose catheter 10 manufactured by USCI/Bard of Billerica, Mass. Two of the lumens (0.61 mm internal diameter) 11 are used for electrical conductors inter-connecting the velocimeter and Doppler transducer 13 attached to the tip of the catheter. The third lumen 12 (1.245 mm internal diameter) may be used for a "J" guide wire and/or for sensing blood pressure. The catheter is also curved at a 30 degree angle relative to its primary axis at a point 4 cm from its tip.

The ultrasonic transducer and display (ultrasonic imaging system) is a Model No. 128XP-10 made by Acuson of Mountain View, Calif. A standard Doppler imaging format was used for color display of anatomical structures causing Doppler frequency shifts.

The Doppler velocimeter, in accordance with the invention, may be especially modified, in a manner well known in the art, to synchronize with the ultrasonic imaging system. At the beginning of an ultrasonic burst from the ultrasonic transducer a synchronization pulse is sent to the Doppler velocimeter. Upon receipt of the synchronization pulse, the Doppler velocimeter may immediately transmit an eight cycle pulse or may delay such transmission for some operator adjustable time period.

It has been determined that the Doppler velocity output from a pulse wave Doppler crystal 13 mounted on the end of the multi-purpose catheter permits non-fluoroscopic catheterization of the aortic root and left ventricle chambers of the heart in a more efficient manner. This method involves advancing the catheter retrogradely from the femoral artery (or brachial artery) while maintaining maximum axial systolic blood flow velocity (blood flowing in an opposing direction to the advancing catheter with the catheter remaining in axial alignment with the blood vessel lumen).

Where a blood vessel branch is inadvertently entered or the catheter tip bends upon itself, Doppler velocity waveform polarity reversal indicates blood flowing away from the catheter tip. Using this information for guidance, the catheter can be subsequently pulled back, rotated and advanced in the direction which maintains maximal axial systolic blood flow, as indicated by the Doppler velocity waveform. Doppler frequency shifts from such structures as the aortic valve lie in the aortic frequency range, making the opening and closing of the aortic valve audible as the catheter approaches. The catheter may be advanced across the aortic valve by orienting the catheter into the region of the outflow tract having the highest systolic velocities.

Figure 2:
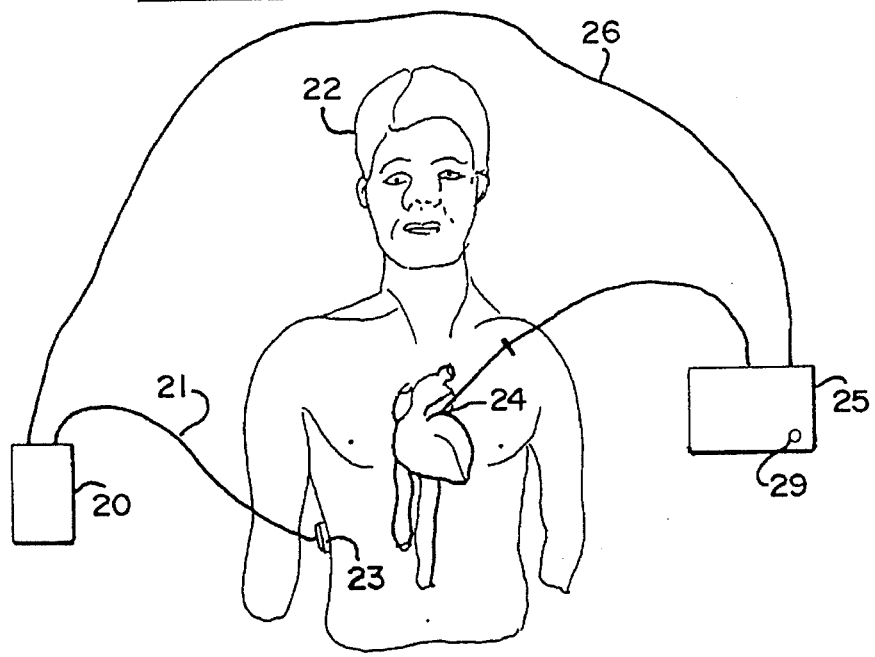
FIG. 2 is a cut-away view of a catheterized subject and catheterization equipment in accordance with the invention.

Turning now to FIG. 2, the catheter tip orientation and positioning system is shown in schematic form in conjunction with an outline 22 of a human subject catheterized in accordance with the invention. As shown, a catheter 27 having a Doppler transducer 24 at an insertion end of the catheter is inserted into the cardiovascular system of the subject 22 through a sheath inserted into an artery for vascular access. The Doppler transducer 24 on the tip of the catheter 27 is interconnected with the velocimeter 25 to monitor flood flow in the catheterized blood vessel during catheterization.

To monitor progress of the catheter tip 24 an ultrasonic imaging system 20, 21, 23, is used. The ultrasound transducer 23 of the ultrasonic imaging system 20, 21, 23 may be used as a transesophageal, intravascular, transthoracic, transabdominal, transgastric, or transcolonic probe. In accordance with the invention, an interconnect 26 provides a synchronization pulse from the ultrasonic imaging system monitor and control unit 20 to the velocimeter control 25.

Used as a transesophageal probe the patient is sedated and an ultrasonic transducer 23 is inserted into the throat of the catheterized subject to a position opposite the heart of the patient. The ultrasonic transducer 23 may then be raised or lowered, or twisted, such that an adequate view of the Doppler transducer 24 is obtained.

In other situations an intravascular probe is used. An intravascular probe is used when ultrasonic imaging is done of the heart from the right atrium which may be entered from the superior or inferior vena cava. Intravascular probes may also be placed in the aorta or left ventricle chambers via the brachial or femoral arteries. In either case the intravascular probe (ultrasonic transducer 23) is inserted through the sheath to an appropriate position within the subject.

Where a transthoracic probe is indicated, an ultrasonic transducer 23 is located on an anterior chest wall of the patient and positionally adjusted as appropriate for an adequate view of the Doppler transducer 23.

Transabdominal, transgastric, or transcolonic probes may be indicated if any of the cardiovascular diagnostic or therapeutic devices are used within abdominal venous or arterial structures.

Figure 3:
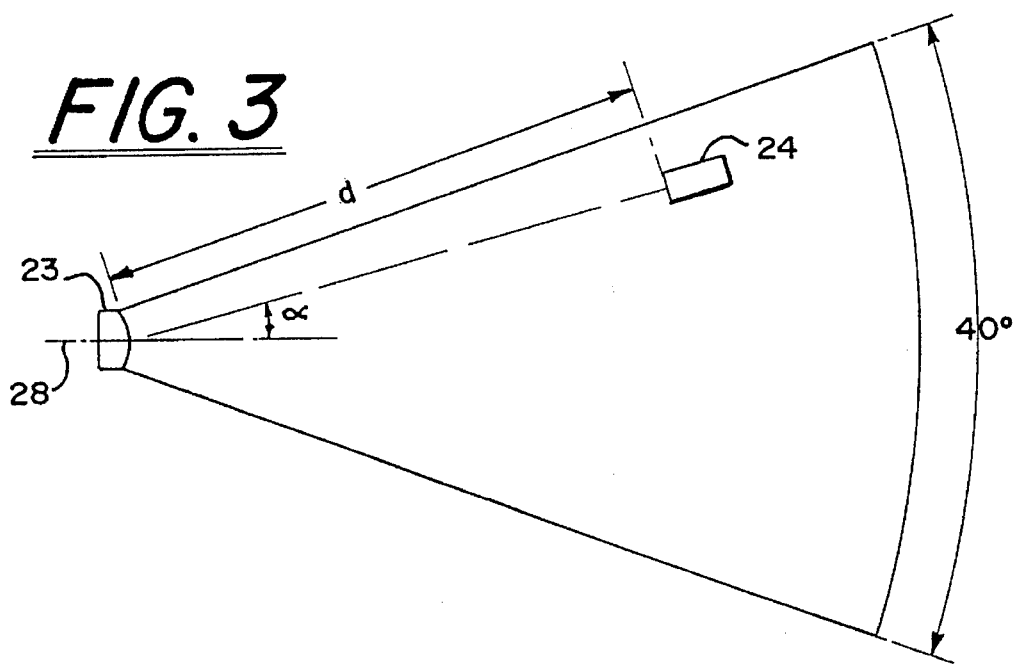
FIG. 3 depicts an ultrasonic imaging system monitor image showing a catheter tip in accordance with the invention.

The ultrasonic imaging system 20, 21, 23 creates an image of the cardiovascular system of the subject 22 by transmitting an ultrasonic pulse from the ultrasonic transducer 23 and then waiting for reflected ultrasonic waves received within a monitored arc (FIG. 3). The ultrasonic imaging system controller 20 determines where to place reflecting objects on a display 20 based upon a receiving angle of a reflected wave and by the elapsed time between transmission of the ultrasonic pulse and receipt of a reflected wave.

As an example, if the ultrasonic transducer 23 were to transmit an ultrasonic pulse and the Doppler transducer 24 (FIG. 3) were at a distance "d" from the ultrasonic transducer, then the transmitted ultrasonic wave would require a time $t_0$ reach the Doppler transducer 24 and be reflected. An additional time period, $t_0$, would also be required for the reflected wave to return to the ultrasonic transducer 23. If the Doppler transducer were at an angle $\alpha$ from the reference axes 28 of the ultrasonic transducer 23, the ultrasonic imaging system controller 20 would use the angle of the reflected wave $\alpha$ and time period for receipt of the reflected wave, $2t_0$, to place an image in the proper location of the display 20.

While the ultrasonic imaging system 20, 21, 23 would display the location of the Doppler transducer 24 in the proper location under the process just described, additional information on Doppler transducer orientation is also displayed in accordance with the invention. The additional information on orientation is provided under the above example by using the described synchronization pulse to cause the Doppler transducer 24 to transmit an eight cycle pulse at a time, $t_0$, after the synchronization pulse. Causing the Doppler transducer 24 to transmit an eight cycle pulse at time, $t_0$, causes the eight cycle pulse to arrive at the ultrasonic transducer 23 at the same instant that a reflected wave from the Doppler transducer 24 is received. Since the eight cycle pulse transmitted by the Doppler transducer 24 is much larger in amplitude than the pulse reflected from the Doppler transducer, the image displayed on the monitor 20 at the location of the Doppler transducer 24 is completely dominated by the eight cycle pulse.

As a result of the receipt of the eight cycle pulse by the ultrasonic transducer 23, a series of brightly colored bars are displayed on the monitor 20 in place of the image of the Doppler transducer 24. When the Doppler transducer 24 is aimed directly at the ultrasonic transducer 23 (0 degree angle), the bars are at their brightest color. When the Doppler transducer is aimed 180 degrees away from the ultrasonic transducer 23, the bars may not appear at all and the Doppler transducer 24 may appear as a conventional ultrasonic image caused by reflection of the acoustic wave from the ultrasonic transducer 23. A determination of orientation at angles from 0 degrees to 180 degrees may be made by comparison of the bars to a set of known color charts or may be performing automatically via a computer which averages the color value and compares the average to a table of values.

In order to determine the delay, $t_0$, after the synchronization pulse for transmission of the pulse from the Doppler transducer 23, the velocimeter 25 may be calibrated in an appropriate fixture (e.g., a tank of water) or the delay 29 may be visually adjusted so that the bars are superimposed over the image of the Doppler transducer 24. Alternatively, the bars may be placed adjacent the image of Doppler transducer 24 so that position and orientation of the Doppler transducer may be simultaneously monitored.

In another embodiment of the invention additional Doppler transducers are attached to the catheter 10 at repeating intervals along the catheter 10 and each connected to its own velocimeter 25. By varying the frequency and burst repetition rate of each 8-cycle burst of each Doppler transducer the respective color bar set of each Doppler transducer could be made to appear as a different color, thereby presenting information on position and orientation at discrete points along the catheter.

In another embodiment of the invention, the velocimeter is not synchronized to the ultrasonic imaging system 20, 21, 23. Without synchronization, the positioning of the bars on the display 20 is based upon the geometric relationship of the positions of the ultrasonic probe 23 and Doppler transducer 24. Even though the positioning of the colored bars is geometric, the bars may still be used under the invention to determine orientation of the Doppler transducer 24.

In another embodiment of the invention two directional acoustic transmitters 13 (FIG. 1) are placed on the insertion end of the probe. The first directional acoustic transmitter 13 transmits an acoustic pulse in synchronism with the ultrasonic transducer 23 (without time delay). The second directional transducer 13 has a variable time day.

The use of two directional acoustic transmitters 13 under the embodiment provides a means by which an operator may be able to easily locate the catheter tip on the monitor 20 of the ultrasonic imaging system in cases where a clear image of the catheter tip does not appear. Since the first directional acoustic transmitter 13 operates without time delay. The color bars of the first directional acoustic transmitter appear at a location on the monitor 20 half-way between the ultrasonic transducer 23 and the tip of the probe. The color bars of the first directional transducer provides a convenient reference point for adjusting the time delay of the second directional acoustic transmitter for placement of the second set of color bars directly over the location of the probe tip.

The use of active acoustic transmissions from the Doppler transducer 24 provides a method of localizing and determining the orientation of an insertion end of a probe not possible with passive prior art devices such as taught by Breyer (U.S. Pat. No. 4,706,681). Also, since the ultrasonic imaging system 20, 21, 23 provides an adjustable scan field depth, the images of the monitor 20 provides a three-dimensional view including orientation that was not possible under the prior art.

We claim:

1. An apparatus for localizing and determining orientation of an insertion end of a probe having therapeutic or diagnostic utility within a biotic structure, such apparatus comprising:

a probe with a directional acoustic transmitter attached to a tip of an insertion end of the probe;

a power supply for energizing the directional acoustic transmitter; and an ultrasonic imaging system having Doppler capability for displaying positional information of the probe and indicia of the orientation of the tip of the probe based upon a signal from the directional acoustic transmitter.

2. The apparatus as in claim 1 further comprising means for synchronizing the directional transmitter with the ultrasonic imaging system.

3. The apparatus as in claim 2 further comprising means for delaying an acoustic transmission of the directional acoustic transmitters with respect to an ultrasonic transmission of the ultrasonic imaging system.

4. The apparatus as in claim 3 further comprising an at least second acoustic transmitter attached to an insertion end of the probe.

5. The apparatus as in claim 4 further comprising means for making non-coincidental the amplitude, carrier frequency, or burst repetition frequency of the ultrasonic imaging system and an excitation signal of the at least second acoustic transmitter.

6. The apparatus as in claim 3 wherein the means for delaying further comprises an adjustable delay.

7. The apparatus as in claim 1 wherein the directional acoustic transmitter further comprises a velocimeter.

8. A method of determining an orientation of an insertion end of a probe having therapeutic or diagnostic utility within a biotic structure, such method comprising the steps of:

transmitting an acoustic signal from a directional acoustic transmitter attached to a tip of the insertion end of the probe; and displaying a representation of the transmitted signal as an indicia of the orientation of the tip of the probe on a display of an ultrasonic imaging system.

9. The method as in claim 8 further comprising the step of determining a blood flow rate and direction past the tip of the probe.

10. The method as in claim 8 further comprising the step of displaying positional information of the probe on the ultrasonic imaging display.

11. The method as in claim 8 further comprising the step of synchronizing the transmitted acoustic signal with transmission from the ultrasonic imaging system.

12. The method as in claim 8 further comprising the step of delaying the transmitted signal with respect to a transmitted acoustic signal of the ultrasonic imaging system.

13. The method as in claim 12 further comprising the step of adjusting the delay of the transmitted signal to place the representation of the transmitted signal adjacent an image of the probe produced by the ultrasonic imaging system.

14. An apparatus for determining orientation of an insertion end of a catheter with respect to a catherized subject, such apparatus comprising:

a directional acoustic transmitter attached to a tip of the insertion end of the catheter;

a power supply for periodically energizing the directional acoustic transmitter for the transmission of an acoustic pulse; and an ultrasonic imaging system for receiving and displaying indicia of the orientation of the tip of the probe based upon the transmitted acoustic pulse.

15. The apparatus as in claim 14 wherein the directional acoustic transmitter and the power supply further comprise a Doppler velocimeter.

16. The apparatus as in claim 14 further comprising means for synchronizing the transmitted acoustic pulse of the directional acoustic transmitter with an ultrasonic pulse of the ultrasonic imaging system.

17. The apparatus as in claim 16 further comprising means for delaying the transmitted acoustic pulse of the directional acoustic transmitter with respect to the transmitted ultrasonic pulse of the ultrasonic imaging system.

18. The apparatus as in claim 17 further comprising means for adjusting the delay of the transmitted acoustic pulse of the directional transmitter.

19. An apparatus for localizing an insertion end of a probe having therapeutic or diagnostic utility within a biotic structure, such apparatus comprising:

a probe with a directional acoustic transmitter attached to a tip of an insertion end of the probe;

a power supply for energizing the directional acoustic transmitter; and an ultrasonic imaging system having Doppler capability for displaying indicia of position of the probe based upon a signal from the directional acoustic transmitter.

20. The apparatus as in claim 19 further comprising means for synchronizing the directional transmitter with the ultrasonic imaging system.

21. The apparatus as in claim 20 further comprising means for delaying an acoustic transmission of the directional acoustic transmitters with respect to an ultrasonic transmission of the ultrasonic imaging system.

22. The apparatus as in claim 21 further comprising an at least second acoustic transmitter attached to an insertion end of the probe.

23. The apparatus as in claim 22 further comprising means for making non-coincidental the amplitude, carrier frequency, or burst repetition frequency of the ultrasonic imaging system and an excitation signal of the at least second acoustic transmitter.

24. The apparatus as in claim 21 wherein the means for delaying further comprises an adjustable delay.

25. The apparatus as in claim 19 wherein the directional acoustic transmitter further comprises a velocimeter.

26. A method of localizing an insertion end of a probe having therapeutic and diagnostic utility within a biotic structure, such method comprising the steps of:

transmitting an acoustic signal from a directional acoustic transmitter attached to a tip of the insertion end of the probe; and displaying indicia of the location of the tip of the probe on a display of an ultrasonic imaging system based upon the transmitted acoustic signal from the directional acoustic transmitter.

27. The method as in claim 26 further comprising the step of determining a blood flow rate and direction past the tip of the probe.

28. The method as in claim 26 further comprising the step of displaying positional information of the probe on the ultrasonic imaging display.

29. The method as in claim 26 further comprising the step of synchronizing the transmitted acoustic signal with transmissions from the ultrasonic imaging system.

30. The method as in claim 26 further comprising the step of delaying the transmitted signal with respect to a transmitted acoustic signal of the ultrasonic imaging system.

31. The method as in claim 30 further comprising the step of adjusting the delay of the transmitted signal to place the representation of the transmitted signal adjacent an image of the probe produced by the ultrasonic imaging system.

32. An apparatus for locating an insertion end of a catheter with respect to a catherized subject, such apparatus comprising:

a directional acoustic transmitter attached to a tip of the insertion end of the catheter;

a power supply for periodically energizing the directional acoustic transmitter for the transmission of an acoustic pulse; and an ultrasonic imaging system for receiving and displaying indicia of the location of the tip of the probe based upon the transmitted acoustic pulse of the directional acoustic transmitter.

33. The apparatus as in claim 32 wherein the directional acoustic transmitter and the power supply further comprise a Doppler velocimeter.

34. The apparatus as in claim 32 further comprising means for synchronizing the transmitted acoustic pulse of the directional acoustic transmitter with an ultrasonic pulse of the ultrasonic imaging system.

35. The apparatus as in claim 34 further comprising means for delaying the transmitted acoustic pulse of the directional acoustic transmitter with respect to the transmitted ultrasonic pulse of the ultrasonic imaging system.

36. The apparatus as in claim 35 further comprising means for adjusting the delay of the transmitted acoustic pulse of the directional transmitter.

* * * * *

UNITED STATES PATENT AND TRADEMARK OFFICE
CERTIFICATE OF CORRECTION

PATENT NO. : 5,546,949
DATED : August 20, 1996
INVENTOR(S) : Leon Frazin, et al.

It is certified that error appears in the above-indentified patent and that said Letters Patent is hereby corrected as shown below:

On the Title Page, in the title, delete "LOGICALIZING" and insert --LOCALIZING--.

Column 1, line 2, delete "LOGICALIZING" and insert --LOCALIZING--.

Signed and Sealed this

Twenty-ninth Day of October 1996

*Attest:*

BRUCE LEHMAN

*Attesting Officer*   *Commissioner of Patents and Trademarks*